United States Patent [19]

Ginnaga et al.

[11] Patent Number: 4,687,738

[45] Date of Patent: Aug. 18, 1987

[54] METHOD FOR THE PRODUCTION OF HA FRACTION CONTAINING PROTECTIVE ANTIGENS OF *BORDETELLA PERTUSSIS* AND *PERTUSSIS* VACCINE

[75] Inventors: Akihiro Ginnaga; Hiroshi Koba; Shin Sakuma; Hisashi Kitagawa; Akira Yamada, all of Kumamoto; Yoji Suzuki, Hino, all of Japan

[73] Assignees: The Chemo-Sero-Therapeutic Res. Inst., Kumamoto; Teijin Limited, Osaka, both of Japan

[21] Appl. No.: 874,670

[22] Filed: Jun. 16, 1986

Related U.S. Application Data

[63] Continuation of Ser. No. 591,169, Mar. 19, 1984, abandoned.

[30] Foreign Application Priority Data

Mar. 30, 1983 [JP] Japan .................................. 58-54680
Apr. 2, 1983 [JP] Japan .................................. 58-58548

[51] Int. Cl.⁴ .......................................... C12P 21/00
[52] U.S. Cl. .......................................... 435/68; 435/3; 435/802; 435/253; 435/822; 435/812; 435/813; 424/92; 424/88; 424/93
[58] Field of Search .................... 435/68, 3, 812, 243, 435/822, 253, 802, 813; 424/92, 93, 88

[56] References Cited

U.S. PATENT DOCUMENTS

| 3,577,319 | 5/1971 | Nielsen et al. | 424/92 |
| 4,468,455 | 8/1984 | Hopkins | 435/3 |
| 4,500,639 | 2/1985 | Suzuki et al. | 435/243 |
| 4,551,429 | 11/1985 | Greenspan | 424/92 |
| 4,563,303 | 1/1986 | Ginnoya et al. | 424/92 |

FOREIGN PATENT DOCUMENTS

| 0201459 | 7/1983 | Fed. Rep. of Germany | 435/3 |
| 0141416 | 11/1980 | Japan | 424/92 |
| 1011687 | 4/1983 | U.S.S.R. | 435/3 |

OTHER PUBLICATIONS

Imaizumi et al, *Inf. and Immun*, 41, 1983, pp. 1183–43, "Effect... Cyclodextran on the Production of Toxin by *B. pertussis*".
Imaizumi et al, "Heptakis(2,6-O-dimethyl)$\beta$-cyclodextran", *J. Clin. Microbiol.*, 17(15), 1983, pp. 781–786.
Imaizumi et al, "A New Culturing Method... *B. pertussis*", *J. Microbiol. Methods*, 2(6), 1984, pp. 339–348.
Stainir et al, "A Simple Chemically Defined Medium... *B. pertussis*", *J. Gen. Microbiol.*, 63, 1971, pp. 211–220.

*Primary Examiner*—John Kight
*Assistant Examiner*—Garnette D. Draper
*Attorney, Agent, or Firm*—Wegner & Bretschneider

[57] ABSTRACT

A method for production of HA fraction containing protective antigens of *Bordetella pertussis* (i.e. a fraction containing F-HA and LPF-HA) in an industrial scale, for instance, with a fermentator, which comprises inoculating a strain of *B. pertussis* in a liquid culture containing a cyclodextrin or its derivative, culturing it by a spinner culture under controlling the culture temperature and the amount of dissolved oxygen and under defoaming condition, optionally under controlling the pH range, and harvesting the produced HA fraction from the culture broth at a stage of from logarithmic growth phase to static grow phase, and a method for production of a pertussis vaccine from the HA fraction thus obtained by formalinizing the HA fraction in the presence of an amino acid.

7 Claims, 6 Drawing Figures

METHOD FOR THE PRODUCTION OF HA FRACTION CONTAINING PROTECTIVE ANTIGENS OF *BORDETELLA PERTUSSIS* AND *PERTUSSIS* VACCINE

This application is a continuation of Ser. No. 591,169, filed Mar. 19, 1984 now abandoned.

The present invention relates to a method for the production of HA fraction containing protective antigens of *Bordetella pertussis,* i.e. a fraction containing F-HA (Filamentous Hemagglutinin) and LPF-HA (Leucocytosis-promoting Factor Hemagglutinin) and a pertussis vaccine from the HA fraction. More particularly, it relates to a method for the production of the HA fraction containing protective antigens of *B. pertussis* which comprises culturing *B. pertussis* in a liquid medium supplemented with a cyclodextrin or its derivative by a spinner culture (This is synonym of shaking culture, aeration culture, and aeration spinner culture) under controlling the temperature and the amount of dissolved oxygen and under defoaming condition and harvesting the produced HA fraction from the culture broth and also to an industrial method for the production of a pertussis vaccine by formalinizing the HA fraction thus harvested in the presence of an amino acid.

Pertussis is one of the infectious diseases and appears frequently in babies and children and hence is very important disease in view of public health. Particularly, babies suffered from this disease occasionally show very heavy symptom and sometimes result in death. It is well known that this disease can be protected by a previous vaccination, and for such a purpose, there is widely used an inactivated vaccine prepared from whole cells of *B. pertussis* phase I. However, the inactivated vaccine containing whole cells has significant side reaction, and hence, inoculation of vaccine had been prohibited temporarily in the past in Japan. The disease in babies and children caused by *B. pertussis* is still one of the most important social problems, and hence, it has been required to develop a pertussis vaccine with no side reaction.

Sato et al had succeeded in the production of precipitated-purified pertussis vaccine which is an epochal acellular vaccine and had been found based on basic study on protective antigens (cf. Japanese Patent Publication No. 5203/1982). This vaccine comprises mainly as the protective antigens HA fraction containing F-HA and LPF-HA and shows excellent protective effect with a little side reaction, and hence, it has already practically been used.

This precipitated pertussis vaccine is prepared by inoculating *B. pertussis* phase I in an appropriate medium, subjecting it to a static culture at about 35° C. for 5 days, centrifuging the culture broth, separating the supernatant fluid, adding ammonium sulfate to the supernatant fluid so as to become about 50 % saturation, separating the resulting precipitates by centrifuging at 10,000 r.p.m. for 30 minutes, extracting the precipitates with a buffer supplemented with sodium chloride, subjecting the extract to a sucrose density gradient centrifugation in a usual manner to collect the pertussis HA fraction and remove endotoxin fraction, and then treating the resulting HA fraction with formalin to make detoxification, and optionally adding to the vaccine thus prepared diphtheria toxoid and tetanus toxoid, optionally followed by adding thereto an aluminum adjuvant and further adding thereto a stabilizer such as gelatin, glucose, etc. to give a combined vaccine of precipitated-purified pertussis antigens, diphtheria toxoid and tetanus toxoid.

This method has, however, a problem in the culture of microorganism in a large scale, and hence, the vaccine is hardly produced in an industrial scale. That is, according to the known method for the preparation of precipitated-purified pertussis vaccine, the culture is carried out in a small vessel such as Roux's bottle containing 100 to 300 ml of a liquid medium at about 35° C. for 5 days under static condition, which method is very small scale and requires very long incubation period of time.

Generally, culture of microorganisms in a large scale is carried out by a spinner culture in a liquid medium using a fermenter. It is reported that *B. pertussis* can fairly propagate in a liquid medium by a shaking culture, but the production of F-HA fraction is very low level (cf. Arai, H. & Munoz, J.J.; Infect. Immun. 25, 764–767, 1979). This means that at least one component of the purified vaccine is hardly produced in a large scale. Thus, although the precipitated-purified pertussis vaccine developed by Sato et al is an excellent vaccine, it must be prepared by a static culture in a small scale consuming very long incubation period of time, and hence, it has been desired to develop an improved method for the production of such a vaccine.

Recently, Suzuki et al had studied on various additives which can promote the growth of *B. pertussis* phase I and also promote the production of LPF-HA, particularly in a synthetic medium, and they had found that addition of cyclodextrins or their derivatives, particularly methylated $\beta$-cyclodextrin (i.e. heptakis 2,6-O-dimethyl-$\beta$ cyclodextrin, hereinafter referred to as "methylated $\beta$-CD") is highly effective on the growth of *B. pertussis* phase I and production of LPF-HA in a synthetic Stainer-Scholte liquid medium (cf. Stainer, D. W. & Scholte, M. J.; J. Gen. Microbiol. 63, 211–220, 1971) by a reciprocal shaking culture and further that the addition of cyclodextrin compound is also effective on stabilization of LPF-HA in the culture broth (cf. Suzuki et al, Symposium on Toxins, proceedings of the 29th symposium on Toxins at Osaka, 1–5, 1982, Jpn. J. Med. Sci. Biol., 36, 111, 1983).

However, when the above method is applied to scaled-up fermentation using a fermentation tank (e.g. a 10 liter or larger volume tank) in order to produce the pertussis vaccine in an industrial scale, it has been found that cell concentration can be increased in rotary shaking culture or reciprocal shaking culture under a constant shaking condition, but the production of LPF-HA is not sufficient, which is unexpected from the common sense in the conventional shaking culture.

In Manual for the production and control of vaccine, Pertussis vaccine, WHO in 1977, there is disclosed a large scale culture of *B. pertussis* using a fermentation tank and the production of pertussis organisms and whole cell vaccine therefrom, wherein the culture is carried out by aerating the medium with surface aeration or through grids and stirring with a particular stirring blade, by which air is embraced in the medium. The present inventors had tried to culture *B. pertussis* in Stainer-Scholte medium or an improved medium as mentioned hereinafter (10 liter volume) in accordance with the method as described in the above mannual of WHO under a constant aeration from the bottom of the vessel, i.e. by aerating in an air volume of 0.2 VVM [volume of air (liter)/volume of culture vessel (liter)]

culture time (minute) at a constant rotation of the stirring blade of 500 to 600 r.p.m. As a result, it has been found that this method is not sufficient for production of HA fraction of B. pertussis while it is fairly effective for increasing the number of cells, and hence, it is not suitable for industrial production of purified pertussis vaccine.

The present inventors have extensively studied on an improved method for the production of HA fraction containing protective antigens of B. pertussis and a pertussis vaccine in an industrial scale and on the culture conditions suitable for not only increase of number of cells but also enhanced production of the desired LPF-HA and F-HA fraction. As a result, it has been found that when the culture is carried out under controlling the amount of dissolved oxygen (hereinafter, referred to as "DO") and under defoaming condition at a certain culture temperature and further optionally under controlling the pH range, not only the cells can remarkably propagate but also the HA fraction of B. pertussis is remarkably increased even in a large culture scale, for example, in a spinner culture using a conventional fermentation tank, and further that when the HA fraction thus obtained is treated with formalin in the presence of an amino acid, it is made detoxificated to give a pertussis vaccine, and even when the vaccine thus prepared is kept at 37° C. for a long period of time, no reversal of toxicity is observed. In this formalin treatment, when an amino acid is present, the resulting atoxic HA fraction can be filtered with a membrane filter because of no production of aggregated precipitate (as observed in the absence of amino acid) and it is not necessary to be subjected to ultrasonic treatment, etc.

An object of the present invention is to provide an improved method for producing HA fraction containing protective antigens of B. pertussis. Another object of the invention is to provide an industrial method for producing the HA fraction in a large scale, e.g. in a conventional fermenter. A further object of the invention is to provide a method for producing a pertussis vaccine in an industrial scale. These and other objects and advantages of the invention will be apparent to persons skilled in the art from the following description.

BRIEF DESCRIPTION OF THE DRAWINGS

FIG. 3 (II) depicts the change in F-HA and LPF-HA as a function of time of Example 6.

FIG. 4 (I) depicts the change in cell concentration as a function of time of Example 7.

FIG. 4 (II) depicts the change in F-HA and LPF-HA as a function of time of Example 7.

According to the present invention, the desired HA fraction can be produced by inoculating B. pertussis in a liquid medium containing a cyclodextrin or its derivative, culturing with aeration and stirring under controlling the temperature in the range of from 20° to 37° C. and also the amount of DO in the range of from 0.7 to 6.0 ppm under defoaming condition and optionally under controlling the pH range in the range of from 6.0 to 9.0, and harvesting the produced HA fraction of protective antigens at the logarithmic growth phase or static growth phase. Besides, the pertussis vaccine is prepared from the HA fraction by formalinizing it in the presence of an amino acid, and preparing the formalinized HA fraction into a purified pertussis vaccine, a precipitated-purified pertussis vaccine or a mixed vaccine of precipitated- purified pertussis vaccine, diphtheria toxoid and tetanus toxoid.

The starting B. pertussis used in the present invention includes any available strains of B. pertussis which are used for preparing a pertussis vaccine. Usually, phase I strain is used after being subcultured in a Bordet-Gengou medium and being cultured by spinner culture. Such cultures are used as a seed culture and are inoculated into a liquid medium. B. pertussis phase II strains can also be utilized. The amount of the seed culture to be inoculated is not critical, but is usually in the range of 0.2 to 10 IOU/ml, preferably about 1.0 IOU/ml, in the final concentration IOU: International Opacity Unit, 1 IOU being $1 \times 10^9$ organisms, cf. W.H.O Technical Reports Series 1979, Vol. 638, page 66, A.3.3.2.

The liquid medium includes any known liquid media, preferably Stainer-Scholte medium, more preferably an modified Stainer-Scholte medium, i.e. Stainer-Scholte medium supplemented with 0.1 to 20 g/l of casamino acids wherein the contents of ascorbic acid and glutathione are controlled to the range of 0.01 to 1 g/l and 0.1 to 5 g/l, respectively (hereinafter, referred to as "modified medium").

The cyclodextrin (abbreviated as CD) or its derivative to be added to the medium includes all isomers of $\alpha$-CD, $\beta$-CD and $\gamma$-CD; etherified derivatives such as methylated $\alpha$-CD, methylated, $\beta$-CD, or methylated $\gamma$-CD; and further aminated derivatives and esterified derivatives, or the like. These CD compounds are used alone or in combination of two or more thereof. Among these compounds, dimethylated $\beta$-CD (heptakis 2,6-O-dimethyl-$\beta$-cyclodextrin), dimethylated $\alpha$-CD (heptakis 2,6-O-dimethyl-$\alpha$-cyclodextrin, trimethylated $\beta$-CD (heptakis 2,3,6-O-trimethyl-$\beta$-cyclodextrin and trimethylated $\alpha$-CD (heptakis 2,3,6-O-trimethyl-$\alpha$-cyclodextrin are most effective. The amount of the CD compounds is not critical, but is usually in the range of 0.001 to 5 g/l preferably about 0.5 to 2.5 g/l.

It has been found by the present inventors that the cell growth of B. pertussis and increase of production of F-HA and LPF-HA in a large scale culture are affected by the culturing temperature and control of DO, the defoamation treatment, and further the control of pH range. These factors are explained below in detail.

Optimum range of the culturing temperature was examined by using, as a seed culture, a subculture of B. pertussis phase I Tohama strain which is harvested from Bordet-Gengou medium, inoculating the subculture (0.2 IOU/ml) into a modified medium (10 ml) containing 1.0 g/l of methylated $\beta$-CD, and culturing it at a temperature of from 17° C. to 42° C., at a reciprocal shaking rate of 60 times/minute for 48 hours by using a temperature gradient culture apparatus TN 112D (manufactured by Toyo Kagaku Sangyo K.K.). The cell concentration was calculated based on the turbidity at optical density of 650 ($OD_{650}$) using a photoelectric colorimeter, Coleman Jr. type 6D (manufactured by Coleman Co.). This experiment was done in a small scale, but at least as to the culture temperature, similar tendency is observed even in a large scale spinner culture using fermenter.

Figure 1:
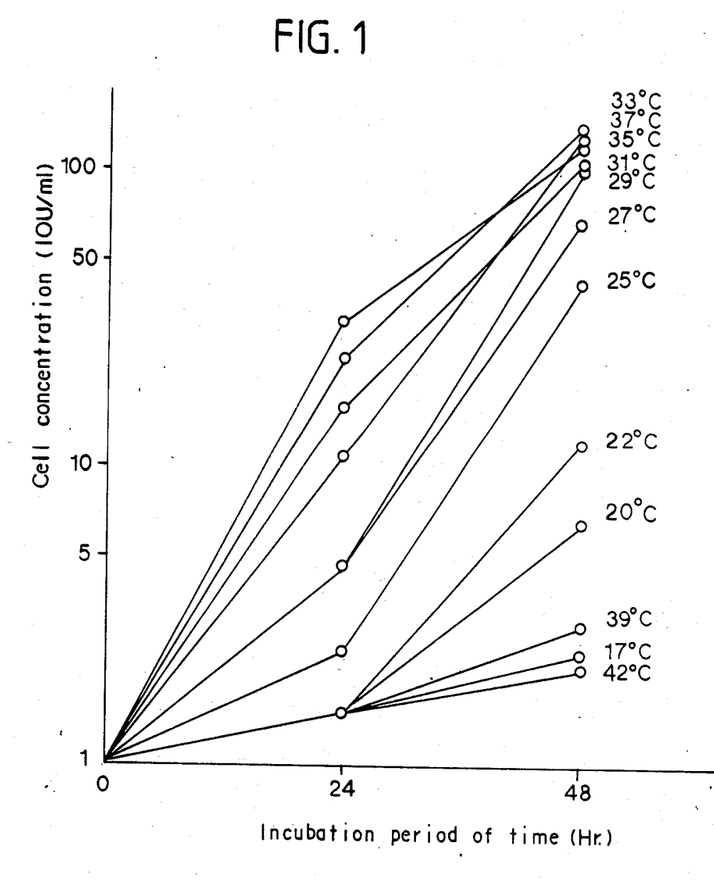
FIG. 1 depicts cell concentration of B. pertussis as a function of incubation time and temperature.
Figure 2:
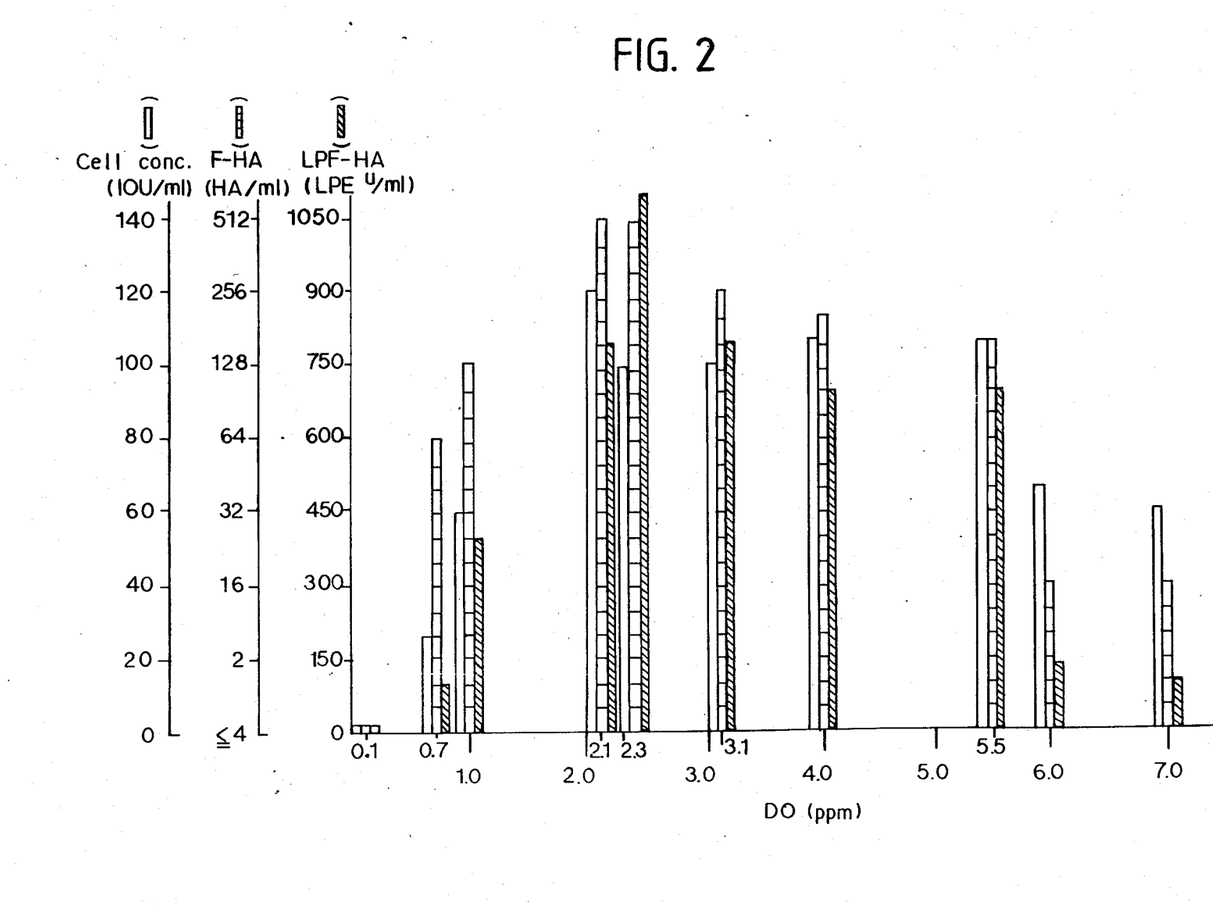
FIG. 2 depicts the cell concentration, F-HA concentration and LPF-HA concentration as a function of DO.

The results are shown in the accompanying FIG. 1. As is shown in FIG. 1, the microorganism can grow well at a culture temperature of from 20° to 37° C., preferably from 23° to 37° C.

The amount of DO in the medium is in the range of from 0.7 to 6.0 ppm, preferably from 1.0 to 5.5 ppm. By controlling the DO to the above range, propagation of B. pertussis is increased, and the production of LPF-HA and F-HA is also significantly increased.

The DO is preferably regulated by controlling the aeration rate and stirring rate. The aeration rate and stirring rate are not specified, but the aeration rate is not more than 3 VVM, usually in the range of from 0.1 to 2 VVM, preferably from 0.1 to 1.5 VVM, and the stirring rate is not more than 600 r.p.m., usually in the range of from 50 to 350 r.p.m., preferably from 100 to 250 r.p.m. When pure oxygen is used together with air, the aeration rate and stirring rate may be decreased.

The growth of the microorganism in the culture broth and the yield of F-HA and LPF-HA are also significantly affected by defoaming treatment. For instance, when the culture is carried out without defoaming under the same conditions as in Example 1 as disclosed hereinafter, the cells adhere to foams and are deposited on the wall of vessel or are exhausted through an air exhaust nozzle, which results in several to 80% decrease of the cell concentration and of the amount of F-HA and LPF-HA. The defoaming may be done by a conventional mechanical defoaming or chemical defoaming, for instance, with a conventional defoaming device such as rotary disc or spray nozzle, or with a chemical defoaming agent such as aliphatic esters (e.g. B-3009A, manufactured by Asahi Electrochemical Co. LTD.), silicon compounds (e.g. KM70, KM72, manufactured by Shinetsu Chemical Co. LTD.); alcohol compounds (e.g. LG109, LG126, manufactured by Asahi Electrochemical Co. LTD.). Mechanical defoaming is more preferable in view of easier recovery and purification of the HA fraction from the culture broth.

Optimum pH range of the medium was determined by culturing *B. pertussis* in media having various pH under the same conditions as in Example 1 except that DO was kept at a constant of 2.5 ppm. As a result, within the range of pH 6.0 to 9.0, the microorganism grew well, and in pH 6.5 to 8.5, particularly in pH 6.8 to 7.5, the rate of growth of the microorganism was also increased to some extent.

The control of the culture temperature, amount of DO, defoaming, and pH range is carried out by automatical control or manual control.

In order to obtain the desired HA fraction in a high yield, it is important to check the growth phase of microorganism, and it is most preferable to harvest the fraction at the stage of from logarithmic growth phase to stationary growth phase via conversion phase. This stage may vary with amounts of the microorganism to be inoculated, but is usually 7 to 40 hours after inoculation. For instance, when 1.0 IOU/ml of the microorganism is inoculated, the suitable culture time is usually 24 to 35 hours.

Using the HA fraction-containing culture broth, a precipitated-purified pertussis vaccine is prepared, for instance, in the following manner.

The culture broth obtained above is used as it stands or it is used after being centrifuged to separate the supernatant fluid. To the culture broth or supernatant fluid is added ammonium sulfate so as to become about $\frac{1}{3}$ saturation, and the resulting precipitates are collected by centrifugation or filtration. The precipitates are dissolved in a phosphate buffer (pH 7.2) containing 1 mole of sodium chloride. To the solution is added ammonium sulfate so as to become about $\frac{1}{2}$ saturation, and the resulting precipitates are separated by centrifugation or filtration. The precipitates are dialyzed against the same buffer as above in a dialyzer tubing The resulting solution is ultra-centrifuged, and the supernatant fluid is subjected to a sucrose density gradient centrifuge, and the supernatant fluid (HA fractions of *B. pertussis*) is collected. The above procedure is preferably carried out at a temperature of 4° C. or lower. The HA fractions thus obtained contain a large amount of the desired LPF-HA and F-HA. According to electrophoresis, the LPF-HA and F-HA thus obtained have similar molecular weight and electrical charge to those of LPF-HA and F-HA obtained by the known static culture of *B. pertussis*, and further have the similar shape (observed with an electron microscope), the same antigenicity (tested by precipitation reaction in gel) and the same LPF toxicity in mouse.

The HA fraction thus obtained is appropriately diluted with a saline, usually in 2 to 3 fold dilution, and thereto is added formalin in a concentration of 0.1 to 1.2 v/v%, preferably 0.4 to 0.8 v/v%, and the mixture is treated at a temperature of 20° to 43° C., preferably 37° to 40° C., for 3 to 60 days. By this formalin treatment, LPF activity and HSF (Histamine-sensitizing factor) activity are decreased to give an atoxic fraction. It has been found by the present inventors that when the formalin treatment is carried out in the presence of an amino acid, the period of time for the formalin treatment is remakedly shortened and further neither aggregated precipitation nor reversal of toxicity are observed. A stabilizer such as Tween 80 or gelatin may optionally be added together with the amino acid. The stibilizer is usually used in an amount of 0.02 to 0.05%.

The amino acid includes glycine, methionine, cysteine, sodium glutamate, aspartic acid, serine, alanine, leucine, valine, threonine, γ-aminobutyric acid, lysine, histidine, etc. which may be used alone or in combination of two or more thereof. The amount of the amino acid is not critical, but is usually in the range of 0.01 to 0.5M, preferably 0.05 to 0.3M.

When the purified HA fraction obtained from the culture broth in the present invention, i.e. after being cultured in a medium containing cyclodextrin or its derivative using a fermenter, is formalinized in the presence of an amino acid, no aggregated precipitates are produced, and hence, it can be filtered with a conventional memberane filter for sterilization. On the contrary, when the formalinization is carried out substantially in absence of an amino acid, aggregated precipitates are produced like in the formalinization of the HA fraction obtained by a conventional stationary culture in a medium containing no cyclodextrin, and hence, it is required to crush with ultrasonic treatment. In this case, it is difficult to pass the fraction through a membrane filter for sterilization.

After the formalinization and filtration as above, the filtrate is regulated so as to have an appropriate concentraion of protein, usually a final concentration of protein nitrogen: 8 to 20 μg TCAPN/ml (TCAPN: hot trichloroacetic acid precipitable protein nitrogen). The solution thus obtained is optionally mixed with diphtheria toxoid and tetanus toxoid, and is precipitated optionally by adding thereto an adjuvant such as aluminum hydroxide or aluminum phosphate in a final concentration of 0.15 to 0.3 μg/ml, and then the resulting precipitates are removed. Finally, a stabilizer such as gelatin or glucose and also a preservative such as thimerosal are added thereto to give the desired vaccine.

The present invention is illustrated by the following Examples, but should not be construed to be limited thereto.

Example 1

A 50 liter fermenter (manufactured by Marubishi Rika K.K.) was charged with a modified medium (35 liters) having the components as shown in Table 1 wherein sterilized methylated β-CD being added in a final concentration of 1.0 g/liter. After inoculating *B. pertussis* phase I in an amount of 1.0 IOU/ml, it was cultured under aeration through bottom of the vessel using a sparger with mechanical defoaming at 35° C., pH 7.2 for 24 hours with varying the amount of DO.

TABLE 1

| Components | Content (g/l) |
|---|---|
| Basal medium* | |
| Sodium glutamate | 10.720 |
| l-Proline | 0.240 |
| Sodium chloride | 2.500 |
| Potassium dihydrogen phosphate | 0.500 |
| Potassium chloride | 0.200 |
| Magnesium chloride | 0.100 |
| Calcium chloride | 0.020 |
| Trishydroxymethylaminomethane | 6.100 |
| Casamino Acids | 10.000 |
| pH | 7.3 |
| Supplemental liquid* | |
| l-Cysteine hydrochloride | 0.040 |
| Ferrous sulfate | 0.010 |
| Ascorbic acid | 0.400 |
| Niacine | 0.004 |
| Glutathione (reduced type) | 0.150 |

*The basal medium was sterilized at 121° C. under high pressure for 30 minutes, and the supplemental liquid was sterilized by membrane filtration, and both were mixed before use.

As to the culture broth thus obtained, the following various factors were measured.

Cell concentration measured in the same manner as described hereinbefore,

F-HA: measured by haemagglutination test (cf. Sato, Y. et al, Infect. Immun. 7, 992–999, 1973), LPF-HA in vitro: the unit (LPEu/ml) is determined by Hp-ELISA method (cf. Sato et al, Jpn. J. Med. Sci. Biol., 35, 135, 1982), and LPF-HA in vivo: measured by intravenously administering LPF-HA to ddY male mice (4 weeks age) and counting number of leucocytes 3 days after the intravenous administration of LPF HA to ddY male mice (4 weeks age). The results are shown in the accompanying FIG. 2.

As is clear from FIG. 2, increased growth of microorganism and enhanced production of HA fraction were observed in the range of DO 0.7 to 6.0 ppm, particularly 1.0 to 5.5 ppm.

REFERENCE EXAMPLES 1 TO 10 AND EXAMPLES 2 TO 5

Production of HA fraction of *B. pertussis* was compared in various culture conditions, particularly between the conventional fermenter wherein both the aeration and agitation being constantly done and the fermenter of the present invention wherein the aeration and agitation being continuously changed.

A 14 liter fermenter (manufactured by NBS Co.) was charged with the same modified medium (10 liters) as used in Example 1 (wherein methylated β-CD was added in a final concentration of 1.0 g/liter) and thereto was inoculated *B. pertussis* phase I in an amount of 1.0 IOU/ml, and then, it was cultured under aerating from the bottom of the vessel using a sparger at 35° C. for 36 hours under the conditions as set forth in Table 2.

In Reference Examples 1–5, 7 and 8 in Table 2, the culture was carried out at a constant aeration and stirring without defoaming treatment, among which the culturing conditions in Reference Example 5 (stirring rate: 100 r.p.m., aeration: 0.5 VVM) gave good production of HA fraction. However, even under such good conditions, although a certain logarithmic growth (cell concentration: about 10 IOU/ml) was achieved till about 10 hours, the rate of growth was rapidly decreased thereafter and, even after 36 hours, the cell concentration was still about 15 IOU/ml and the production of HA fractions was also so low (F-HA: 16 HA/ml, LPF-HA: 100 LPEu/ml). Even when the culture was continued for 48 hours, neither cell concentration nor production of HA fraction was almost increased.

In Reference Examples 7 and 8, the culture was carried out at a constant stirring of 500 r.p.m. or 600 r.p.m. with aeration rate of 0.2 VVM without defoaming treatment. In bothe cases, after 5 to 10 hours, cells adhered onto the upper wall of vessel or the culture both flowed out from the vessel due to vigorous foaming, and even though all cells remained within the vessel, adhered on the wall and also flowed out one were collected after 36 hours, the production of HA fraction was significantly low.

In Reference Example 10, the culture was carried out under controlling DO but without defoaming treatment. In this culture, there were similarly observed the flowing out of culture broth and adhesion of cells onto the wall, and the production of HA fraction was extremely low.

In Reference Examples 6 to 9, the culture was carried out at a constant aeration and stirring with defoaming treatment. In all cases, the DO amount at the initial stage of culture was more than 6.0 ppm which is not suitable for production of HA fraction. With progressing the culture, the DO decreased sequentially, and before 36 hours, it became lower than 0.7 ppm which is not suitable for propagation of cells and also for the production of HA fraction.

In Reference Example 9, wherein a chemical defoaming being carried out, after 36 hours, the cell concentration became 80 IOU/ml, but F-HA and LPF-HA were 128 HA/ml and 500 LPEu/ml, respectively In Examples 2 to 5, the culture was carried out under controlling the DO within a range of 1.6 to 3.5 ppm by controlling automatically and continuously the aeration and stirring rate with a DO controller (manufactured by NBS Co.) with defoaming treatment. In all Examples, even after 10 hours, the microorganism grew in logarithmic phase and after 36 hours, high levels of cell concentration, F-HA and LPF-HA were obtained.

By the way, when aeration was done from surface, no production of HA fraction was observed.

TABLE 2

| Constant or varying aeration and agitation | Example | Aeration VVM | Stirring r.p.m | Control of DO[1] ppm | Defoaming[2] | Produced amount after 36 hours culture | | |
|---|---|---|---|---|---|---|---|---|
| | | | | | | IOU/ml | HA/ml | LPEU/ml |
| Constant aeration and stirring | Ref. Ex. 1 | 0.05 | 50 | — | — | 8 | 4 | 0 |
| | Ref. Ex. 2 | 0.10 | 100 | — | — | 7 | 4 | 0 |
| | Ref. Ex. 3 | 0.50 | 50 | — | — | 8 | 4 | 0 |
| | Ref. Ex. 4 | 0.50 | 300 | — | — | <1 | <4 | 0 |
| | Ref. Ex. 5 | 0.50 | 100 | — | — | 15 | 16 | 100 |
| | Ref. Ex. 6 | 0.50 | 100 | — | + | 30 | 128 | 90 |
| | Ref. Ex. 7 | 0.20 | 500 | — | — | 30 | 16 | 50 |
| | Ref. Ex. 8 | 0.20 | 600 | — | — | 10 | <4 | 0 |
| | Ref. Ex. 9 | 0.20 | 600 | — | *+ | 80 | 128 | 500 |
| Continuous varying aeration and stirring | Ref. Ex. 10 | Auto[3] | Auto | +(2.5~3.5) | — | 30 | 16 | 50 |
| | Ex. 2 | Auto | 100 | +(2.4~2.8) | + | 120 | 512 | 1100 |
| | Ex. 3 | 0.50 | Auto | +(1.6~3.2) | + | 100 | 512 | 1000 |
| | Ex. 4 | Auto | Auto | +(2.3~2.6) | *+ | 120 | 512 | 1100 |
| | Ex. 5 | Auto | Auto | +(1.7~1.9) | + | 120 | 1024 | 1300 |

[1] +: under controlling, —: under non-controlling
[2]*+: with chemical defoaming agent, Other +: by mechanical defoaming
[3]Auto means that they were automatically changed so as to control the DO as shown.

As is clear from the above results, in a fermenter without DO control, growth of cells was observed when defoamation was done, but even in such case, the productivity of F-HA and LPF-HA was still very low. On the other hand, when the culture was carried out under DO control, not only growth of cells but also production of F-HA and LPF-HA were significantly increased. Thus, in a fermenter, by DO control, growth of cells is increased and further the production of the desired HA fraction of B. pertussis is significantly enhanced.

REFERENCE EXAMPLE 11 AND EXAMPLES 6 AND 7

The culture of the present invention wherein it was carried out under specific conditions in order to produce the desired HA fraction of B. pertussis and the conventional static culture was compared as shown in Table 3. Each culture was carried out as shown below, except that the inoculation amount of microorganism and the culture temperature were 1.0 IOU/ml and 35° C., respectively commonly in both culture.

(A) Static culture (Reference Example 11)

Culture vessel: 1.5 liter volume Roux's bottle
Medium: The same modified medium (0.2 liter) as used in Example 1
Incubation period of time: 120 hours (B) Culture under specific control (the present invention) (Examples 6 and 7)

Culture vessel: 300 liter fermenter (manufactured by Marubishi Rika K.K.)
Medium: The same modified medium (200 liters) as used in Example 1, supplemented with 1.0 g/liter of methylated β-CD (Example 6) and with 1.0 g/liter of methylated α-CD (Example 7)
DO control: 2.2 to 2.4 ppm
Deforming: Mechanical defoaming with rotary disc
pH control: pH 7.3
Incubation period of time: 35 hours
The above results are shown in Table 3.

TABLE 3

| | Static culture | Spinner culture by fermenter (the present invention) | |
|---|---|---|---|
| | | Example 6 | Example 7 |
| Addition of methylated α-(or β-) CD | No | Yes | Yes |
| Cell concentration (IOU/ml) | 85 | 210 | 210 |
| Amount of F-HA (HA/ml) | 1024 | 1024 | 1024 |
| Amount of LPF-HA (LPEu/ml) | 150 | 2350 | 1600 |
| Time (hour) until Stationary growth phase | 120 | 35 | 35 |

As is clear from Table 3, the method of the present invention is far greater than the conventional static culture in the propagation of cells and the LPF-HA production and is the same or higher in the F-HA production. For instance, the method of the present invention is 2 to 3 times higher than the static culture in the cell concentration, and 10 times or higher in the LPF-HA level. Besides, the incubation period of time was significantly shortened, i.e. from 120 hours to 35 hours, in the present invention.

Figure 3:
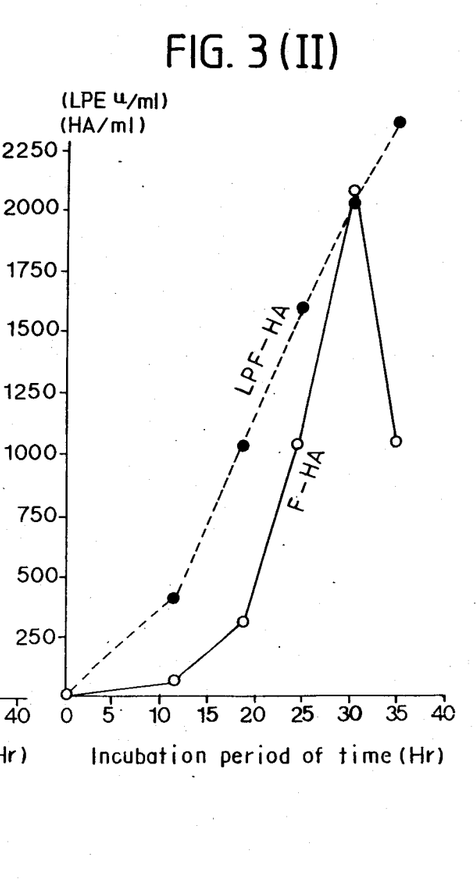
Figure 3I:
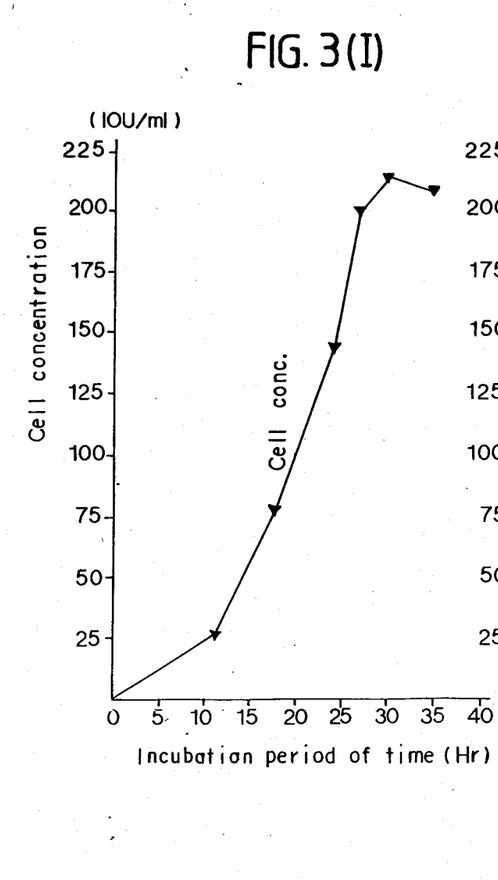
FIG. 3(I) depicts the change in cdll concentration as a function of time of Example 6.
Figure 4:
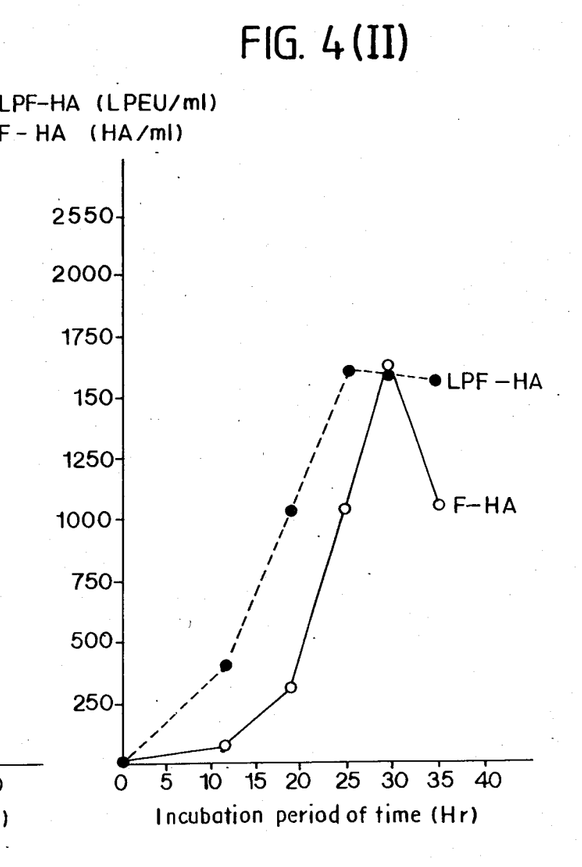
Figure 4I:
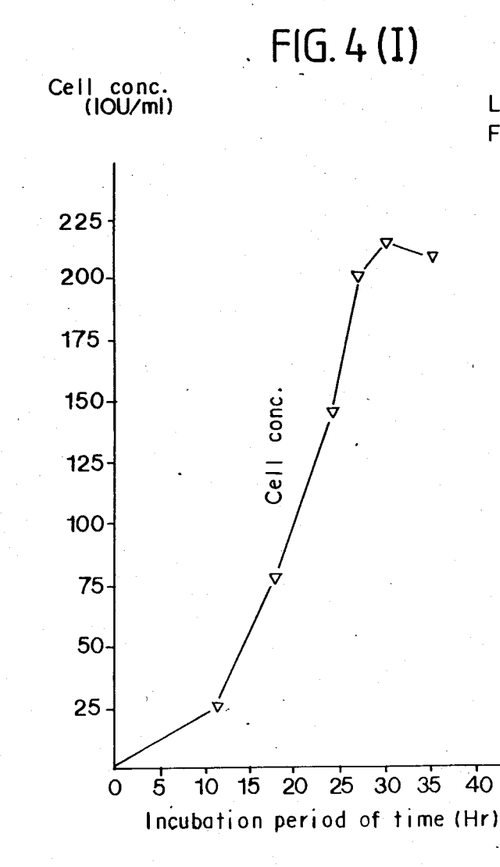

The change of time course of cell concentration, F-HA and LPF-HA levels in the culture under DO control in Examples 6 and 7 are shown in the accompanying FIGS. 3(I) and (II) and FIGS. 4(I) and (II), respectively. As is clear from these Figures, the culture under DO control in the present invention can give increased cell concentration and also significantly increased F-HA and LPF-HA production.

EXAMPLE 8

The HA fraction obtained in Example 1 was diluted with physiological saline so as to become a protein concentration of 30 μg TCAPN/ml. To the solution was added formalin in a concentration of 0.6 or 1.0 v/v% and the mixture was treated at 37° C. or 39° C. for 5 to 21 days. In this formalinizing step, various amino acids as shown in Table 4 were added in a concentration as shown therein.

During the formalin treatment, aggregated precipitate was markedly appeared, and then the solution was dialyzed with a dialyzer tubing in order to remove formalin and then residual toxicity of the product was tested in mice. Besides, after being kept at 37° C. for 3 weeks, reversal of toxicity was also tested. The potency of the vaccines was also tested. These results are shown in Table 4.

solved materials were removed by centrifugation at 10,000 r.p.m. for 30 minutes. To the resulting supernatant fluid was added ammonium sulfate so as to become

TABLE 4

| Conditions for formalinization | | | | | Aggregated precipitates during formalini-zation | Toxicity in mice after removal of formalin | | Toxicity in mice after keeping at 37° C. for 3 weeks | | Potency of vaccine[1] (IPU/ml)*** |
|---|---|---|---|---|---|---|---|---|---|---|
| Amino acid added | | Temp. (°C.) | Conc. of formalin (%) | Days (day) | | LPF u/ml | HSF u/ml | LPF u/ml | HSF u/ml | |
| Kind | concentration | | | | | | | | | |
| — | 0 | 39 | 0.6 | 5 | + | o* | o | •* | • | 11.0 |
|  |  | 39 | 0.6 | 7 | + | o | o | • | • | 10.5 |
|  |  | 39 | 0.6 | 10 | + | o | o | • | • | 8.0 |
|  |  | 39 | 0.6 | 14 | + | o | o | • | • | 8.0 |
|  |  | 39 | 0.6 | 21 | + | o | o | • | • | ND** |
| Glycine | 0.250 | 39 | 0.6 | 5 | — | o | o | o | o | 13.0 |
|  | 0.250 | 39 | 0.6 | 7 | — | o | o | o | o | 11.5 |
|  | 0.250 | 39 | 0.6 | 10 | — | o | o | o | o | 13.0 |
|  | 0.250 | 39 | 0.6 | 14 | — | o | o | o | o | 10.0 |
|  | 0.250 | 39 | 0.6 | 21 | — | o | o | o | o | ND |
| Lysine | 0.025 | 39 | 0.6 | 5 | — | o | o | o | o | 10.0 |
|  | 0.025 | 39 | 0.6 | 7 | — | o | o | o | o | 8.0 |
|  | 0.025 | 39 | 0.6 | 10 | — | o | o | o | o | 8.0 |
|  | 0.025 | 39 | 0.6 | 14 | — | o | o | o | o | 8.0 |
|  | 0.025 | 39 | 0.6 | 21 | — | o | o | o | o | ND |
| Serine | 0.250 | 39 | 0.6 | 7 | — | o | o | o | o | 10.0 |
| Methionine | 0.250 | 39 | 0.6 | 7 | — | o | o | o | o | 9.0 |
| Cysteine | 0.250 | 39 | 0.6 | 7 | — | o | o | o | o | 8.0 |
| Sodium glutamate | 0.250 | 37 | 0.6 | 14 | — | o | o | o | o | 10.0 |
| Aspartic acid | 0.250 | 39 | 1.0 | 5 | — | o | o | o | o | 9.0 |
| Glycine + Serine | 0.150 0.150 | 39 | 0.6 | 7 | — | o | o | o | o | 10.0 |

[1] Each vaccine (8 g TCAPN/ml) was precipitated by aluminum hydroxide in a final concentration of 0.2 mg/ml.
*o: Passed the national control tests, •: Not passed the tests
**ND: Not determined
***IPU: International productive unit

EXAMPLE 9

B. pertussis Phase I Tohama strain which was obtained by culturing in Bordet-Gengou medium was used as a seed culture. The seed culture was inoculated into the same modified medium (0.4 liter) as used in Example 1 which was supplemented with 10 mg/ml of methylated β-CD in a 2 liter flask in a final cell concentration of 1.0 IOU/ml. Incubation was carried out by rotary shaking at 200 rpm at 35° C. for 18 hours to give a seed culture.

The cultures obtained above were pooled and inoculated into the same medium as above (200 liter) in a 300 liter fermenter (manufactured by Marubishi Rika K.K.) in an amount of 1.0 IOU/ml, and it was cultured with aeration and agitation.

The culture was carried out under controlling automatically the aeration and agitation rate so as to make the DO within the range of 1.8 to 2.7 ppm. Besides, other conditions were automatically controlled so as to be the culture temperature: 35° C. and pH: 7.2, and further, the defoamation was mechanically done with a rotary disc.

After culturing for 35 hours, the culture broth was collected. As to the culture broth, the cell concentration and amount of HA fraction were measured. As a result, it showed a cell concentration: 210 IOU/ml, F-HA: 1,024 HA/ml, and LPF-HA: 2,400 LPEu/ml.

The culture broth was centrifuged, and the supernatant fluid was collected. To the supernatant fluid was added ammonium sulfate so as to become ⅓ saturation, and the resulting precipitates were collected by centrifugation at 10,000 r.p.m. for 30 minutes. The precipitates were dissolved in a phosphate buffer (pH 7.2) supplemented with 1 mole of sodium chloride and the undissolved materials were removed by centrifugation at 10,000 r.p.m. for 30 minutes. To the resulting supernatant fluid was added ammonium sulfate so as to become about ½ saturation. The resulting precipitates were collected by centrifugation likewise and were again dissolved in the same buffer as above and dialyzed at 4° C. in a dialyzer tubing, and the undissolved materials were removed by centrifugation likewise. The solution was super-centrifuged and the supernatant fluid was subjected to 10 to 30% sucrose density gradient centrifuge (at 39,000 r.p.m. for 20 hours), and then, HA fractions were collected. The HA fractions were pooled and sterilized by filtering through a membrane filter. The protein concentration of the HA fraction was diluted with the same buffer as above in 30 μg TCAPN/ml. The above steps of the treatment of the collected culture broth and the purification of the HA fraction were carried out at 2° to 4° C.

To the HA fraction obtained above were added 0.6 v/v% of formalin, 0.05 v/v% of Tween 80, 0.02 w/v% of gelatin and 0.25M of glycine, and the mixture was kept at 39° C. for 7 days. The mixture was dialyzed against a phosphate buffer (pH 7.2) supplemented with 0.7 w/v% of sodium chloride in a dialyzer tubing to remove formalin, and the resulting solution was diluted with the same buffer as above so as to make a protein concentration in 8 μg TCAPN/ml to give a diluted solution of an atoxic HA fraction.

To the diluted solution was added an aluminum hydroxide gel in an amount of 0.20 mg/ml (converted to aluminum), by which the HA fraction was adsorbed onto the aluminum gel, to which was added 0.01 w/v% of thimerosal as a preservative to give the desired precipitated-purified pertussis vaccine.

The properties of the vaccine thus obtained were tested in accordance with the national control tests (cf.

Minimum Requirement of Biological Products, Ministry of Health and Welfare, Japan, #287, 1981). As a result, all properties thereof were satisfactory as shown in Table 5.

TABLE 5

| Item | Result |
| --- | --- |
| Content of protein nitrogen (μg/ml) | 8 |
| Sterility test | Passed |
| Staining test | Passed |
| Hydrogen ion concentration | 6.8 |
| Test for freedom from heat-labile toxin | Passed |
| Test for mouse body weight-decreasing toxicity (BWDU/ml) | Passed 7.2 (2.9-14.0) |
| Test for mouse leucocyte-increasing toxicity (LPU/ml) | Passed 0.82 (0.42-1.25) |
| Test for mouse histamine sensitizing toxicity (HSU/ml) | Passed 0.06 (0.01-0.16) |
| Pyrogen test (total temp. °C. in two) | Passed, 0.4 |
| Content of aluminum (μg/ml) | 0.168 |
| Content of thimerosal (w/v %) | 0.0090 |
| Content of formaldehyde (w/v %) | 0.0020 |
| Test for freedom from abnormal toxicity: | |
| In mice | Passed |
| In guinea pig | Passed |
| Potency test (IPU/ml) | Passed, 13.5 |

EXAMPLE 10

To the diluted solution of atoxic HA fraction obtained in Example 9 were added diphtheria toxoid (33 LF/ml) and tetanus toxoid (5 Lf/ml), and thereto was added an aluminum hydroxide gel (0.20 mg/ml, converted to aluminum), by which the HA fraction and toxoids were adsorbed onto the aluminum gel. To the mixture were added 0.02 w/v% of gelatin and 0.1 w/v% of glucose as a stabilizer and further 0.01 w/v% of thimerosal as a preservative to give the desired mixed vaccine of a precipitated-purified pertussis vaccine, diphtheria toxoid and tetanus toxoid.

The properties of the combined vaccine thus obtained were tested in accordance with the national control tests (cf. Minimum Requirement of Biological Products, Ministry of Health and Wellfare, Japan, #287, 1981). As a result, all properties thereof were satisfactory as shown in Table 6.

TABLE 6

| Item | Result |
| --- | --- |
| Content of protein nitrogen (μg/ml) | 28.0 |
| Sterility test | Passed |
| Staining test | Passed |
| Hydrogen ion concentration | 6.72 |
| Test for freedom from heat-labile toxin | Passed |
| Test for mouse body weight-decreasing toxicity (BWDU/ml) | Passed 9.3 (4.2-17.2) |
| Test for mouse leucocyte increasing toxicity (LPU/ml) | Passed 0.66 (0.33-1.02) |
| Test for mouse histamine sensitizing toxicity (HSU/ml) | Passed 0.04 (0.01-0.12) |
| Pyrogen test (total temp. °C. in two) | Passed, 0.5 |
| Content of aluminum (μg/ml) | 0.174 |
| Content of thimerosal (w/v %) | 0.0094 |
| Content of formaldehyde (w/v %) | 0.0020 |
| Test for freedom from abnormal toxicity: | |
| In mice | Passed |
| In guinea pig | Passed |
| Sterility test | |
| In rabbit | Passed |
| In guinea pig | Passed |
| Potency test | |
| Pertussis vaccine (u/ml) | Passed, 13.4 |
| Diphtheria toxoid (u/ml) | Passed, 48.4 |
| Tetanus toxoid (u/ml) | Passed, 44.2 |

What is claimed is:

1. A method for the large scale production of HA fraction containing protective antigens of *Bordetella pertussis*, which comprises inoculating a strain of *B. pertussis* in a liquid medium containing a compound selected from the group consisting of methylated α-cyclodextrin, methylated β-cyclodextrin, methylated γ-cyclodextrin, α-cyclodextrin, β-cyclodextrin, and γ-cyclodextrin, and a combination of two or more thereof, culturing it in a spinner culture at a culture temperature of 20° to 37° C., at an amount of dissolved oxygen of 1.0 to 5.5 ppm under defoaming conditions, separating the culture broth at the stage of from logarithmic growth phase to static growth phase.

2. A method according to claim 1, wherein the liquid medium contains 0.1 to 20 g/liter of Casamino Acids, 0.01 to 1 g/liter of ascorbic acid, 0.1 to 50 g/liter of glutathione and 0.001 to 5 g/liter of a cyclodextrin or its derivative.

3. A method according to claim 1 wherein the culture is carried out for 7 to 40 hours.

4. A method according to claim 1, wherein the defoaming is carried out by a mechanical defoaming.

5. A method according to claim 1, wherein the defoaming is carried out with a chemical defoaming agent.

6. A method according to claim 1, wherein the culture is carried out at a pH 6.0 to 9.0.

7. A method according to claim 1, wherein the culture broth separated at the stage of from logarithmic growth phase to static growth phase is centrifuged to isolate a supernatant containing F-HA and LPF-HA.

* * * * *